(12) United States Patent
Lai

(10) Patent No.: US 6,256,365 B1
(45) Date of Patent: Jul. 3, 2001

(54) APPARATUS AND METHOD FOR RECONSTRUCTION OF IMAGES IN A COMPUTED TOMOGRAPHY SYSTEM USING OBLIQUE SLICES

(75) Inventor: Ching-Ming Lai, Wakefield, MA (US)

(73) Assignee: Analogic Corporation, Peabody, MA (US)

( * ) Notice: Subject to any disclaimer, the term of this patent is extended or adjusted under 35 U.S.C. 154(b) by 0 days.

(21) Appl. No.: 09/375,347

(22) Filed: Aug. 16, 1999

(51) Int. Cl.[7] ....................................................... A61B 6/03
(52) U.S. Cl. ................................. 378/4; 378/17; 378/901
(58) Field of Search ............................. 378/4, 8, 15, 17, 378/901

(56) References Cited

U.S. PATENT DOCUMENTS

| | | | |
|---|---|---|---|
| 5,469,486 | * 11/1995 | Hu et al. | 378/4 |
| 5,651,043 | * 7/1997 | Tsuyuki et al. | 378/65 |
| 5,802,134 | 9/1998 | Larson et al. | 378/4 |
| 5,881,122 | * 3/1999 | Crawford et al. | 378/4 |

OTHER PUBLICATIONS

Feldkamp, L. A., et al., "Practical Cone–Beam Algorithm", J. Opt. Soc. Am., vol. 1, No. 6, Jun. 1984, pp. 612–619.

Yan, X., et al., "Cone–Beam Tomography With Circular, Elliptical And Spiral Orbits", Phys. Med. Biol. vol. 37, No. 3, Nov. 1991, pp. 493–506.

Schaller , S., et al., "New Efficient Fourier–Reconstruction Method For Approximate Image Reconstruction In Spiral Cone–Beam CT At Small Cone Angles", SPIE, vol. 3032, Feb. 1997, pp. 213–325.

Wang, G., et al., "A General Cone Beam Algorithm", IEEE, vol. 12, Sep. 1993m pp. 486–496.

Kudo, H., et al., Helical–Scan Computed Tomography Using Cone–Beam Projections, Journal of Electronics, Information, And Communication Society, J74–D–II, 1991, pp. 1108–1114.*

* cited by examiner

*Primary Examiner*—David V. Bruce
(74) *Attorney, Agent, or Firm*—McDermott, Will & Emery

(57) ABSTRACT

An apparatus and method for reconstructing image data for a region are described. A radiation source and an array of detectors located on opposed sides of a region are used to generate scan data for the region from a plurality of diverging radiation beams, i.e., a cone beam. The cone beam scan data for the region are converted into parallel beam scan data. The reordered parallel beam scan data are used to generate image data for a set of oblique image slices for the region, wherein the oblique image slices form a non-perpendicular angle with the longitudinal axis of the region.

26 Claims, 9 Drawing Sheets

APPARATUS AND METHOD FOR RECONSTRUCTION OF IMAGES IN A COMPUTED TOMOGRAPHY SYSTEM USING OBLIQUE SLICES

FIELD OF THE INVENTION

The present invention relates generally to computed tomography (CT) imaging and more particularly to three-dimensional CT imaging with improved efficiency and reduced image artifacts.

BACKGROUND OF THE INVENTION

FIG. 1 is a schematic axial view of a conventional third generation CT scanner which includes an x-ray source 12 and an x-ray detector system 14 secured to diametrically opposite sides of an annular shaped disk 16. The disk 16 is rotatably mounted within a gantry support (not shown), so that during a scan the disk 16 continuously rotates about a longitudinal z-axis while x-rays pass from the source 12 through an object, such as a patient 20, positioned on a patient table 56 within the opening of the disk 16. The z-axis is normal to the plane of the page in FIG. 1 and intersects the scanning plane at the mechanical center of rotation 18 of the disk 16. The mechanical center of rotation 18 of the disk corresponds to the "isocenter" of the reconstructed image.

In one conventional system, the detector system 14 includes an array of individual detectors 22 disposed in a single row in a shape of an arc having a center of curvature at the point 24, referred to as the "focal spot," where the radiation emanates from the x-ray source 12. The source 12 and array of detectors 22 are positioned so that the x-ray paths between the source and each detector all lie in a "scanning plane" that is normal to the z-axis. Since the x-ray paths originate from what is substantially a point source and extend at different angles to the detectors, the diverging x-ray paths form a "fan beam" 26 that is incident on the detector array 14 in the form of a one-dimensional linear projection. The x-rays incident on a single detector at a measuring interval during a scan are commonly referred to as a "ray," and each detector generates an output signal indicative of the intensity of its corresponding ray. The angle of a ray in space depends on the rotation angle of the disk and the location of the detector in the detector array. Since each ray is partially attenuated by all the mass in its path, the output signal generated by each detector is representative of the attenuation of all the mass disposed between that detector and the x-ray source, i.e., the attenuation of the mass lying in the detector's corresponding ray path. The x-ray intensity measured by each detector is converted by a logarithmic function to represent a line integral of the object's density, i.e., the projection value of the object along the x-ray path.

The output signals generated by the x-ray detectors are normally processed by a signal processing portion (not shown) of the CT system. The signal processing portion generally includes a data acquisition system (DAS) which filters the output signals generated by the x-ray detectors to improve their signal-to-noise ratio (SNR). The output signals generated by the DAS during a measuring interval are commonly referred to as a "projection," "projection profile," or "view" and the angular orientation of the disk 16, source 12 and detector system 14 corresponding to a particular projection profile is referred to as the "projection angle."

If the detector array consists of N detectors, then N projection values are collected at each rotation angle. With the rays in a fan shape, these N projection values are collectively called a fan-beam projection profile of the object. The data of fan-beam projection profiles are often reordered or rebinned to become parallel-beam projection profiles. All rays in a parallel-beam profile have the same angle, called the parallel-beam projection view angle $\phi$. The image of the object can be reconstructed from parallel-beam projection profiles over a view angle range of 180°.

During a scan, the disk 16 rotates smoothly and continuously around the object being scanned, allowing the scanner 10 to generate a set of projections at a corresponding set of projection angles. In a conventional scan, the patient remains at the constant z-axis position during the scan. When obtaining multiple scans, the patient or the gantry is stepped along the longitudinal z-axis between scans. These processes are commonly referred to as "step-and-shoot" scanning or "constant-z-axis" (CZA) scanning. Using well-known algorithms, such as the inverse Radon transform, a tomogram may be generated from a set of projections that all share the same scanning plane normal to the z-axis. This common scanning plane is typically referred to as the "slice plane."

A tomogram is a representation of the density of a two-dimensional slice along the slice plane of the object being scanned. The process of generating a tomogram from the projections is commonly referred to as "reconstruction," since the tomogram may be thought of as being reconstructed from the projection data. The reconstruction process can include several steps including reordering to form parallel-beam data from the fan-beam data, convolution to deblur the data, and back projection in which image data for each image pixel is generated from the projection data. In CZA scanning, for a particular image slice, all the projections share a common scanning plane, so these projections may be applied directly for convolution and to the back projector for generation of a tomogram.

The step-and-shoot CZA scanning approach can be a slow process. During this time consuming approach, the patient can be exposed to high amounts of x-ray radiation. Also, as the scanning table is moved between each scan, patient motion can result, causing motion and misregistration artifacts which result in reduced image quality.

Several approaches have been developed to decrease the time required to obtain a full scan of an object. One of these approaches is helical or spiral scanning in which either the object being scanned or the gantry supporting the x-ray source and detectors is translated along the z-axis, while the disk 16 with source 12 and linear detector array 14 are rotated about the patient. In helical scanning, the projections are normally acquired such that the z-axis position is linearly related to the view angle. This form of helical scanning is commonly referred to as constant-speed-helical (CSH) scanning.

FIG. 2A illustrates the data collected during a conventional CZA scan, and FIG. 2B illustrates the data collected during a CSH scan. As shown in FIG. 2A, if the x-ray source 12 and the detector system 14 are rotated about the object 20 while the object remains at a fixed z-axis location, the scanning planes associated with all the projections collected by the detector system 14 will all lie in a common slice plane 50. As shown in FIG. 2B, if the object 20 or gantry is continuously translated in the direction of the z-axis while the disk is rotated about the object 20, none of the scanning planes will be coplanar. Rather, the scanning plane associated with each projection will lie at a unique position along the z-axis at a locus point on a helical set of loci. FIG. 2B illustrates the z-axis coordinate of the scanning planes corresponding to helical projection angles in the interval (0, 10$\pi$).

In CZA scanning, all the projections share a common scanning plane, so these projections may be applied to the back projector after convolution to generate a tomogram. In CSH scanning however, each projection has a unique scanning plane located at a unique z-axis coordinate, so CSH projections may not be applied to a back projector. However, the data collected during a CSH scan can be interpolated in various fashions to generate a set of interpolated projections that do all share a common scanning plane extending normal to the z-axis. Each interpolated projection, for example, may be generated by combining two projections taken at equivalent projection angles and at different z-axis positions. These interpolated projections may be treated as CZA data and applied after convolution to a back projector to generate a tomogram.

CSH scanning requires some form of interpolation to generate a tomogram, and atomograms generated by CSH scanning therefore tend to be characterized by image artifacts. Also, since the CSH scan projection data, which are collected over an interval of z-axis locations, are combined to generate the interpolated CZA scan data, tomograms generated during CSH scanning have a wider effective slice plane width and, therefore, lower z-axis resolution, than tomograms generated by CZA scanning. However, helical scanning advantageously permits rapid scanning of a large volume of a patient. For example, in a time interval short enough to permit a patient comfortably to hold his or her breath (and thereby remain relatively motionless), a helical scan can collect enough data to fully scan an entire organ such as a kidney.

Another approach to decreasing scan time over CZA scanning is commonly referred to as "cone-beam scanning," in which a three-dimensional volume of the object or patient is scanned at once. In cone-beam scanning, the detection system includes a two-dimensional array of detectors instead of the one-dimensional array used in conventional scanning. The x-ray output from the source diverges in two dimensions to produce the equivalent of multiple fan beams, referred to as a "cone beam," along the zaxis dimension which illuminate multiple rows of plural detectors and therefore form a two-dimensional projection on the array.

In one form of a cone-beam system, the patient or object is maintained in a stationary z-axis position while the source and two-dimensional detector array are rotated around the patient or object. The patient is then moved to a new z-axis position, and the scan is repeated. In this type of step-and-shoot or "stationary cone beam" system, rather than sweeping out a plane, a volume of the object is scanned. After one volume is scanned, the source and detector are stepped along the z-axis to scan the next volume. Still another approach used to decrease scan time is helical cone-beam (HCB) scanning, in which a cone-beam configuration, i.e., a source and two-dimensional detector array, are rotated around the patient while the patient or gantry is continuously translated in the z-direction.

One approach to reconstructing volumetric image data is to divide it into a stack of slices. Standard two-dimensional reconstruction techniques, such as 2D filtered back projection (FBP), are used to reconstruct CZA and interpolated CSH data in non-cone-beam systems. FBP requires that the set of projections used for reconstruction of slices lie in the same plane. This condition is satisfied in CZA scanning, and interpolation is used in CSH scanning to produce a set of interpolated or simulated linear projections which effectively meet this requirement. In either case, 2D FBP is an efficient means of producing image data from the 1D fan beam projection data.

In cone-beam geometry, the required condition is only satisfied for a detector row coplanar with the source in a plane perpendicular to the z-axis, i.e., the center detector row. An image data slice perpendicular to the z-axis will be referred to herein as a normal slice. Other slices, i.e., slices which form a non-perpendicular angle with the z-axis, are referred to herein as oblique slices or tilted slices. In cone-beam CT, a 1D projection defined by the source and a given detector row will intersect a different slice in the object as the gantry rotates. For a helical cone beam scan, no slice is coplanar with the rays in all view angles. Conventional 2D FBP can be used to reconstruct cone-beam data by treating each row as an independent 1D projection. This approximation ignores the cone-beam geometry and results in image artifacts such as streaks and lowering of the reconstructed density.

The approximation can be improved by selecting certain oblique slices for the 2D reconstruction. One such approach is described in U.S. Pat. No. 5,802,134, entitled "Nutating Slice CT Image Reconstruction Apparatus and Method," of the same assignee as the present application. The contents of that patent are incorporated herein in their entirety by reference. In the approach described in the '134 patent, a 2D fan-beam projection profile can be interpolated from the cone-beam data for each slice at each rotation angle. The slice can be reconstructed from the fan-beam projection profiles over sufficient number of rotation angles. In this prior method, the projection profiles are interpolated directly from the actual cone-beam data. The mathematical relation between the interpolated rays of a projection profile and the original rays are complex. Because of this complexity, the prior method included a procedure based on computer simulation of scanning the oblique slice to determine the locations of interpolating rays. The result of the simulation depends on the accuracy of simulation.

An approximate method used to reconstruct cone-beam data is known as the Feldkamp algorithm and is described in L. A. Feldkamp, et al., "Practical cone-beam algorithm," *J. Opt. Soc. Am.* 1, pp. 612–619, (1984).

In the Feldkamp algorithm, the rays are back projected in the three-dimensional cone. Algorithms such as Feldkamp, which attempt to incorporate the true cone-beam geometry of the data, are referred to as three-dimensional filtered back projection (3D-FBP) algorithms. Three-dimensional algorithms reconstructing HCB data have also been developed. Examples of these algorithms are described in the following papers.

1. H. Kudo and T. Saito, "Three-dimensional helical-scan computed tomography using cone-beam projections," *Journal of Electronics, Information, and Communication Society*, J74-D-II, 1108–1114, (1991).

2. D. X. Yan and R. Leahy, "Cone-beam tomography with circular, elliptical and spiral orbits," *Phys. Med. Biol.* 37, 493–506, (1992).

3. S. Schaller, T. Flohr and P. Steffen, "New efficient Fourier reconstruction method for approximate image reconstruction in spiral cone-beam, CT at small cone angles," *SPIE International Symposium on Medical Imaging*, February, 1997.

4. G. Wang, T-H Lin, P. Cheng and D. M. Shinozaki, "a general cone beam algorithm," *IEEE Trans. Med. Imag.* 12, 486–496, (1993).

SUMMARY OF THE INVENTION

The present invention is directed to a method and apparatus for reconstructing image data for a region having a longitudinal axis. A radiation source and an array of detectors are located on a opposed sides of the region. The radiation source emits radiation toward the array of detectors to generate a plurality of diverging radiation beams received by the array of detectors. At least one of the radiation source and the array of detectors is rotatable about the longitudinal axis through a plurality of projection angles to scan the region to generate diverging beam scan data for the region. The diverging beam scan data for the region is converted into parallel beam scan data. At least one image data slice for the region is defined such that the image data slice is oblique with respect to the longitudinal axis. At least a portion of the parallel beam scan data for the region is used to generate image data for the at least one oblique image data slice.

In one embodiment, the array of detectors is a two-dimensional array of detectors. In this embodiment, the plurality of diverging radiation beams form a cone-beam of radiation. In this embodiment, the invention is applicable to diverging beam scan data acquired by helical cone beam scanning.

An angle formed by the oblique image data slice and the longitudinal axis is selected such that the image data slice is coplanar with the radiation source for at least one projection angle. In particular, in one embodiment, the angle of the oblique slice is selected such that the slice is coplanar with the radiation source for three projection angles. Specifically, the image slice can be selected such that it is coplanar with the radiation source at projection angles of 0°, 90° and 180°.

In one embodiment, the image data for the at least one oblique image slice is generated using parallel beam scan data for a ray that intersects the at least one oblique image slice. In one particular embodiment, the ray intersects the middle of the oblique image slice. In another particular embodiment, the image data for the at least one oblique image slice is generated using parallel beam scan data for a plurality of rays that intersect the at least one oblique image slice. In that embodiment, the plurality of rays can be weighted according to the locations at which they intersect the at least one oblique image slice. For example, the weighting scheme can apply a higher weight or priority to beams that intersect at or near the middle of the oblique image slice and lower weights or priorities to rays intersecting the oblique image slice further from the middle.

In accordance with the invention, image data can also be generated for normal image slices, i.e., image slices perpendicular to the longitudinal axis, using the image data generated for the at least one oblique image slice. Image data for multiple oblique image slices can be used in accordance with the invention to generate image data for multiple normal image slices. The image data for the normal image slices can then be used to generate an image of the region.

The oblique slice approach of the invention provides advantages over prior approaches. The use of an oblique slice as opposed to a normal slice reduces errors and, therefore, substantially reduces artifacts in the produced image. The angle of the oblique slice selected in one embodiment of the invention allows the slice to be coplanar with the radiation source from multiple projection angles, resulting in reduced image artifacts. Also, because the image data for the oblique slice is generated using parallel-beam scan data, computational complexity of the approach is substantially less than that of prior systems.

BRIEF DESCRIPTION OF THE DRAWINGS

The foregoing and other objects, features and advantages of the invention will be apparent from the following more particular description of preferred embodiments of the invention as illustrated in the accompanying drawings in which like reference characters refer to the same parts throughout the different views. The drawings are not necessarily to scale, emphasis instead being placed upon illustrating the principles of the invention.

DETAILED DESCRIPTION OF PREFERRED EMBODIMENTS OF THE INVENTION

In the present invention, cone-beam projection data acquired from a helical scan with constant translation speed are first reordered or rebinned into parallel-beam data. The data collected by each row of detectors are thus reordered into parallel-beam projections. One or more image data slices are defined such that each image data slice is oblique to the rotation axis of a scanner. The projection profiles of each oblique slice are then interpolated from these reordered projection data for 2D reconstruction.

In order for a slice to be coplanar with the rays in all view angles, the focal spot or source must lie on the plane of that slice at all view angles. However, no slice can meet that requirement in a helical scan with constant translation speed. Thus, in accordance with the present invention, instead of looking for a perfect coplanar slice, a slice most coplanar with the rays is selected for reconstruction. Projection profiles are interpolated from the collected data to best represent that slice.

More specifically, in accordance with the invention, a stack of oblique slices at successive z locations is selected.

If the interpolated projection profiles were perfectly coplanar with the slices, the images would be reconstructed as accurate as a conventional system with a single row of detectors. Since the slices do not meet a perfect coplanar condition, the reconstruction of images is still an approximation. The reconstruction error depends on the size of the cone angle $2\beta_{max}$, the angle subtended by the beam in the y' z' plane shown in FIGS. 3–5 and 7. For a system with a small cone angle, the reconstruction error can be negligible.

Figure 1:
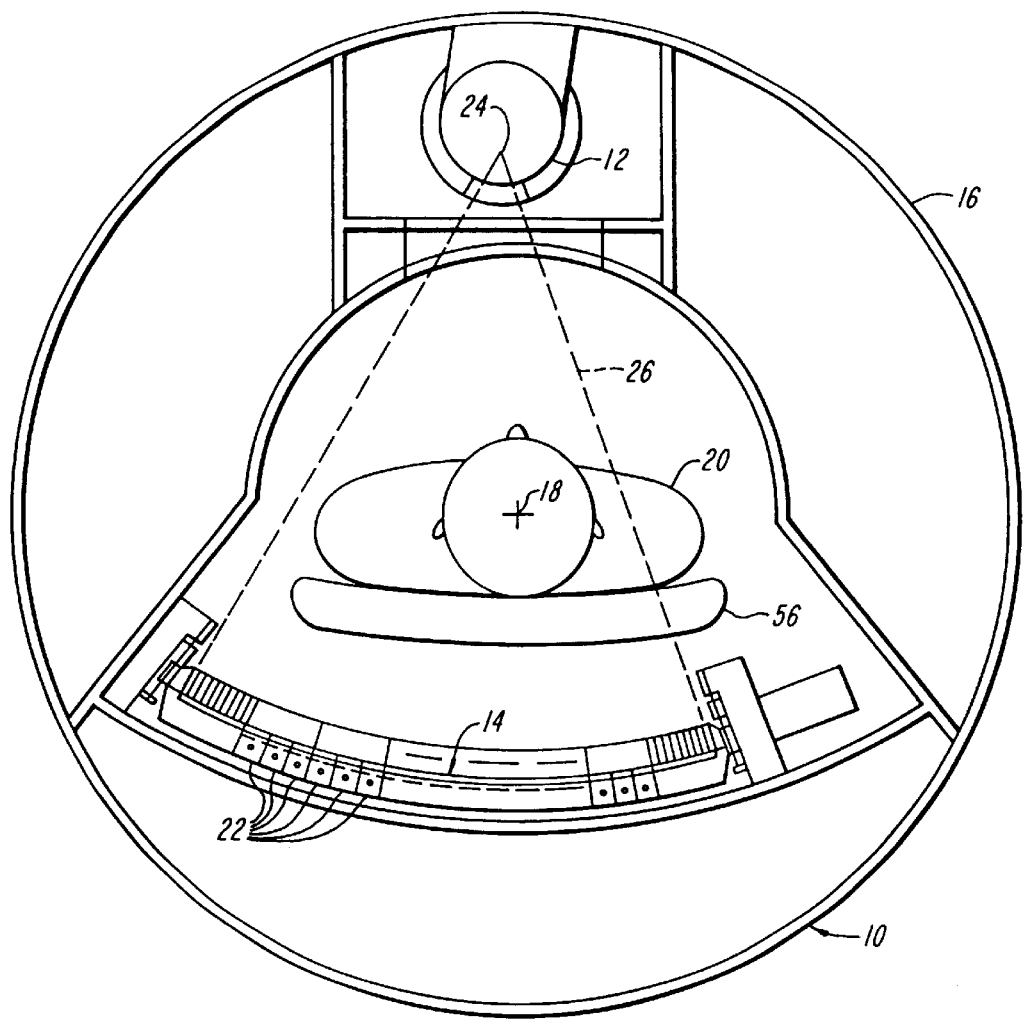
FIG. 1. is a schematic axial view of a typical computed tomography (CT) scanning system.
Figure 2A:
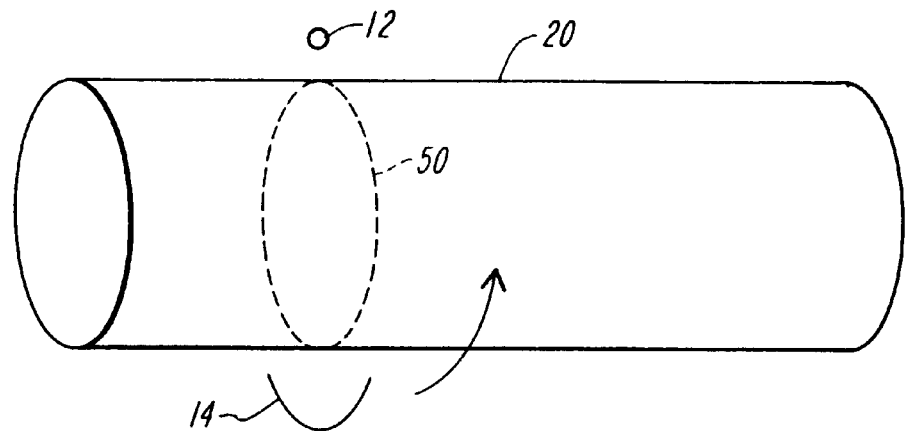
FIG. 2A illustrates the scanning path for a constant z-axis (CZA) scanning mode in a CT scanning system.
Figure 2B:
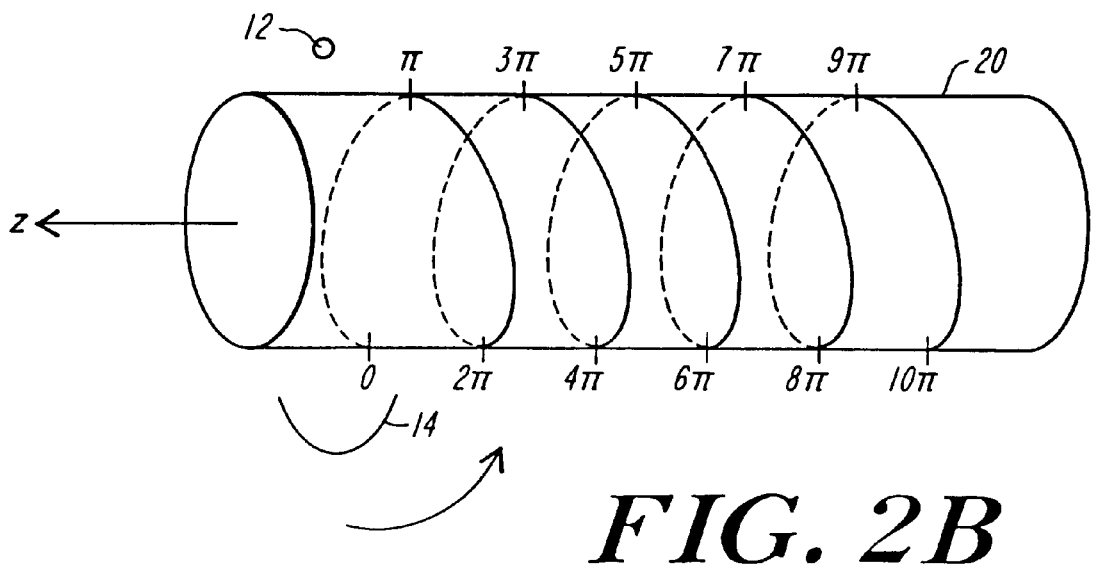
FIG. 2B illustrates the scanning path for constant-speed-helical (CSH) scanning in a CT scanning system.
Figure 3:
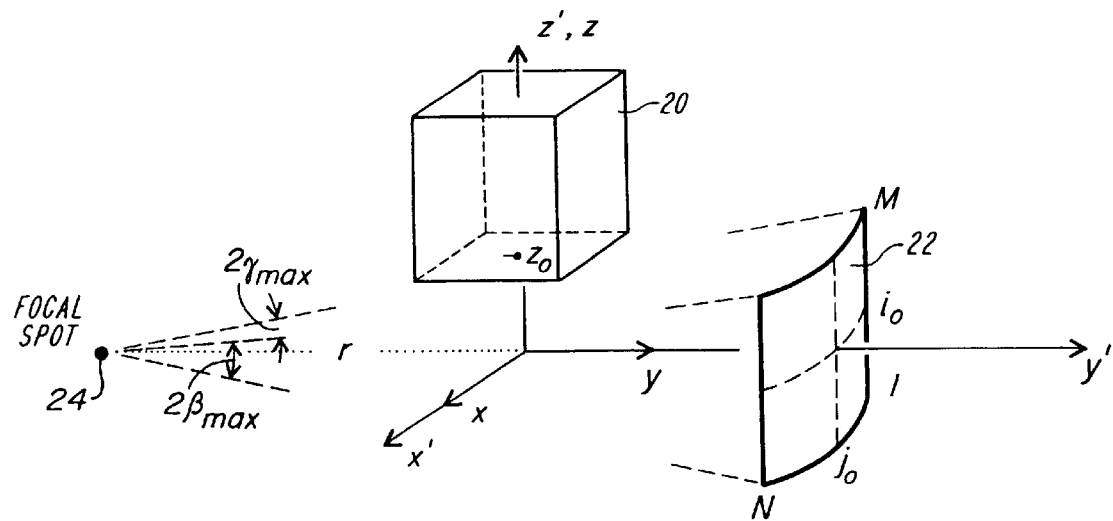
FIG. 3 is a schematic diagram which illustrates a scan object, the focal spot and detector array in a CT scanning system in accordance with the invention.
Figure 4:
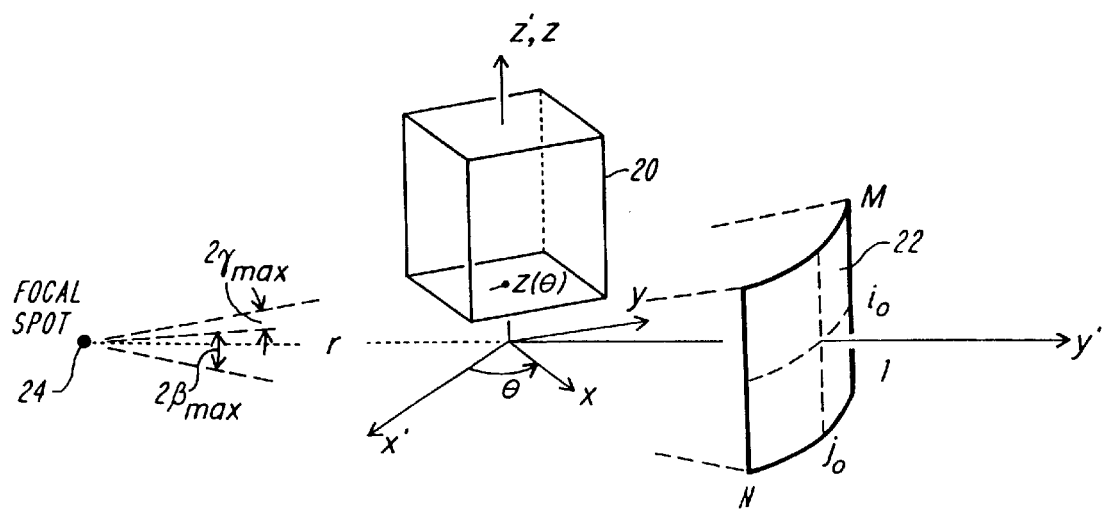
FIG. 4 is a schematic diagram which illustrates the system of FIG. 3 with 45 degrees of rotation.

FIG. 3 contains a schematic diagram illustrating a location and orientation of a scanning object 20 with respect to the focal spot 24 and the detector array 22 in a rotating frame at a starting rotation angle of $\theta=0$, including a 3D matrix representing the image intensity of the scanning object 20. The focal spot 24 and the detector array 22 are fixed in a rotating frame defined by rectangular coordinates x'y'z', while the 3D matrix is referenced to a laboratory frame defined by rectangular coordinates xyz with the first slice located at $z=z_0$. Assuming, as seen in FIGS. 3 and 4, the rotating frame is rotating relative to the laboratory frame clockwise during a scan, the 3D matrix fixed relative to the laboratory frame is then rotating counterclockwise with respect to the rotating frame. During a helical scan, the 3D matrix is traveling at a constant speed along the −z direction with respect to the laboratory frame. The geometry of the 3D matrix at rotation angle of $\theta=45°$, for instance, is depicted in FIG. 4 as viewed in the rotating frame. The pitch of a helical scan is defined as the translation distance traveled by the object 20 relative to the laboratory frame during 360° rotation. If the pitch is 2p, the first slice of the 3D matrix is then located at $$z(\theta)=z_o-p\theta/\pi \quad (1)$$

The detector array 22 includes M rows of detectors. For each row, there are N detectors, or channels. Detectors from the same channel of different rows constitute a column. Thus, the detector array can also be described as N columns of detectors. Usually, N is much greater than M. The N rays measured by each row of detectors will be referred to herein as a transverse fan, since they are radiated from the focal spot 24 and lie on a plane substantially transverse to the z-axis. The M rays measured by each column of detectors will be referred to as a longitudinal fan, since they are also radiated from the focal spot 24 but lie on a plane parallel to the z-axis. The fan angle of a transverse fan is $2\gamma_{max}$, in the order of about 60° as in a convention single-row detector system. The fan angle of a longitudinal fan is the cone angle $2\beta_{max}$, which is in the order of a few degrees. The cone beam system can be considered as having M transverse fans arranged in a small longitudinal fan angle and N longitudinal fans arranged in a large transverse fan angle.

Figure 5:
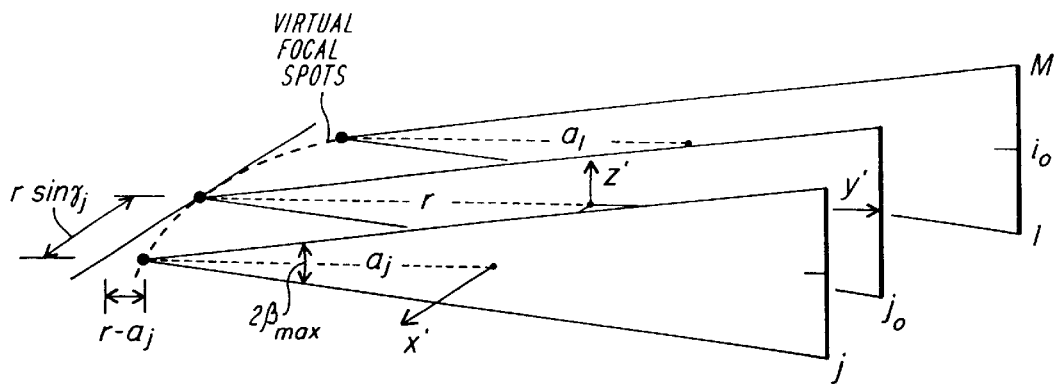
FIG. 5 is a schematic diagram which illustrates reordered rays consisting of N longitudinal fans in parallel, in accordance with the invention.

At each rotation angle, the data of a transverse fan comprises a fan-beam projection profile, as in a conventional single-row detector system. Each projection value in the projection profile is measured along the ray at an angle $\gamma_j$ relative to the ray of the central channel. It is preferable to reorder each fan-beam projection profile into a parallel-beam projection profile, as in parallel-beam reconstruction of 2D image for a single-row detector system. The reordering is performed on each row independent of the data in other rows. The reordered rays consist of N longitudinal fans in parallel, as shown in FIG. 5 for a step-and-shoot scan. In FIG. 5, the focal spot of the central fan is located at y'=−r, while the focal spot of a typical fan $j>j_o$ is located at $y'=-a_j$, with $a_j<r$. Each parallel longitudinal fan is a virtual fan mapped from an existing longitudinal fan in the actual cone-beam configuration. Thus, reordered rays contain N virtual focal spots and have a contour of a wedge shape.

Figure 6:
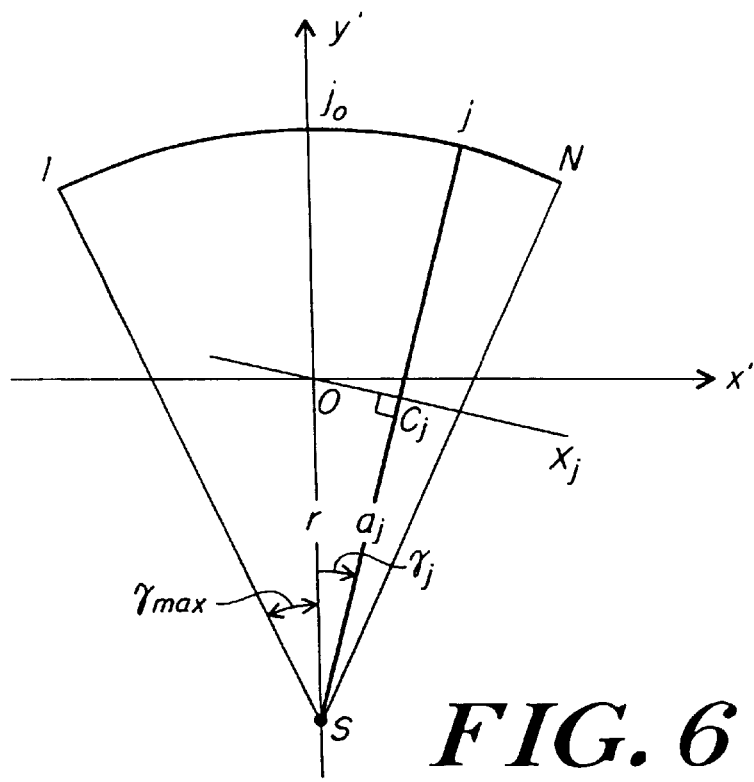
FIG. 6 is a detailed schematic illustration of a central transverse fan of FIG. 5, in accordance with the invention.

The exact location of a virtual longitudinal fan j with respect to the central longitudinal fan $j_o$ can be seen from the central transverse fan shown in FIG. 6, where each ray is the central ray of a longitudinal fan. In FIG. 6, the line $OX_j$ is normal to the longitudinal fan j with $C_j$ being the intersecting point, and it is mapped into the x'-axis of the reordered geometry in FIG. 5. The distance $\alpha_j$ is the distance between the focal spot S and the point $C_j$, with $$\alpha_j = r \cos \gamma_j = r \cos((j-j_o)\delta) \quad (2)$$

where $\delta$ is the angular spacing between adjacent detector channels which gives the angle $\gamma_j=(j-j_o)\delta$. The distance $OC_j$ is the distance between a longitudinal fan j and the central longitudinal fan $j_o$. It is equal to $r \sin \gamma_j$, or $r \sin((j-j_o)\delta)$. Because the distance $\alpha_j$ depends on j, the virtual focal spots in the reordered geometry are not lying on a straight line. Also, the virtual longitudinal fans are not located at equal interval along the x'-axis, as the result of nonlinear dependence of $OC_j$ on j.

Figure 7:
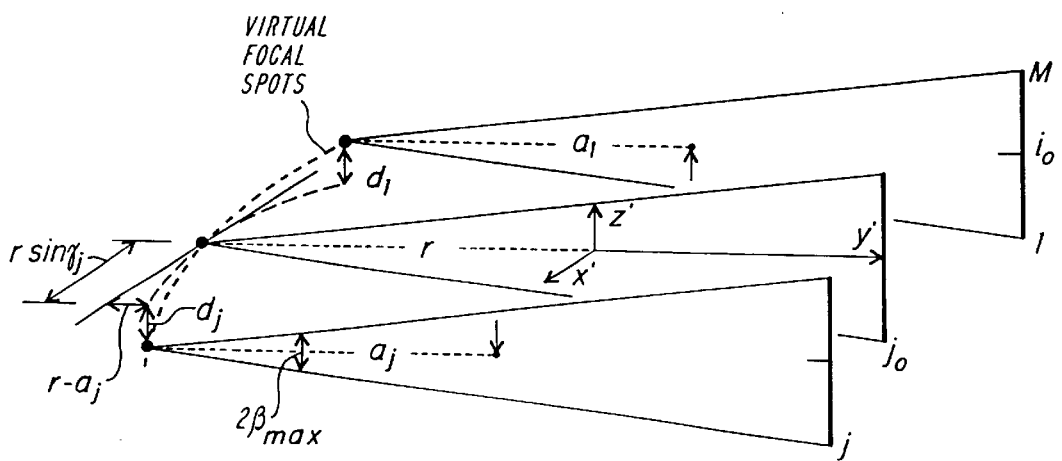
FIG. 7 is a schematic diagram of reordered rays from a helical scan illustrating slight distortion from wedge shape due to translation along the longitudinal axis.

The reordered rays of a helical scan are slightly distorted from the wedge shape, as shown in FIG. 7 at the view angle of $\phi=0°$. Unlike a step-and-shoot scan, the virtual longitudinal fans, while parallel, are no longer at the same z position. This is because the data of each virtual longitudinal fan are actually collected at a different time from the others. The central longitudinal fan (of column $j_o$) is the only one collected at rotation angle of $\theta=0°$. The first virtual longitudinal fan (of column j=1) is collected at a time ahead of rotation angle $\theta=0°$, and it is offset from the central fan in the +z direction. Similarly, the last virtual longitudinal fan (of column j=N) is collected at a time after the rotation angle $\theta=0°$, and therefore it is offset from the central fan in the −z direction. If the pitch of the helical scan is 2p, the offset for the virtual longitudinal fan j in z direction is given by $$d_j = -p\gamma_j/\pi = -p(j-j_o)\delta/\pi \quad (3)$$

When a slice is selected for reconstruction, the projection value of the slice in channel j is derived from the longitudinal fan j. In general, more than one ray of the longitudinal fan intersect the slice. The ray passing the middle point of the slice can be considered as nearest to the slice, and it will be the ray to be interpolated from that longitudinal fan.

Figure 8:
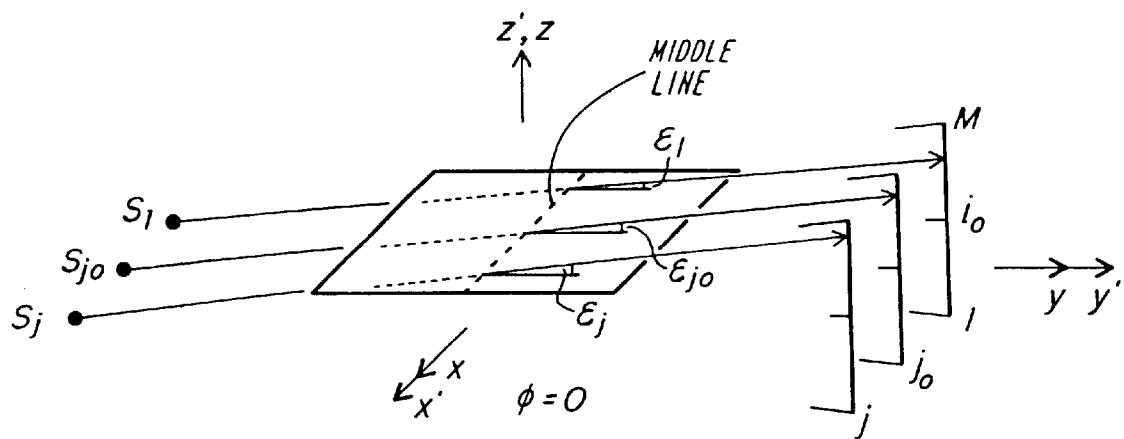
FIG. 8 is a schematic diagram illustrating aberration angles in a normal slice.

There are N middle points on the slice, one for each longitudinal fan. These middle points define a middle line, which is a line on the slice passing the z-axis and perpendicular to the longitudinal fans. Its orientation varies with the view angle. Suppose a normal slice is selected for convolution. The middle line is the line y=0 at view angle of $\phi=0°$, as shown in FIG. 8. The angle between the slice and the ray intersecting the middle line is referred to as the aberration angle. It varies with the channel and the view angle. The aberration angle of channel j is illustrated in FIG. 8 as $\epsilon_j$.

Figure 9A:
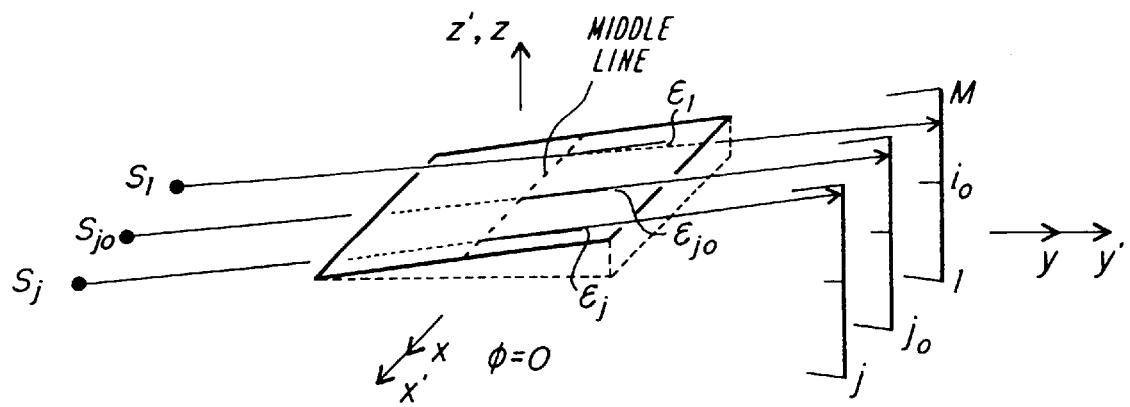
FIGS. 9A and 9B are schematic diagrams illustrating aberration angles in an oblique slice at view angles of 0 and 90 degrees, respectively.
Figure 9B:
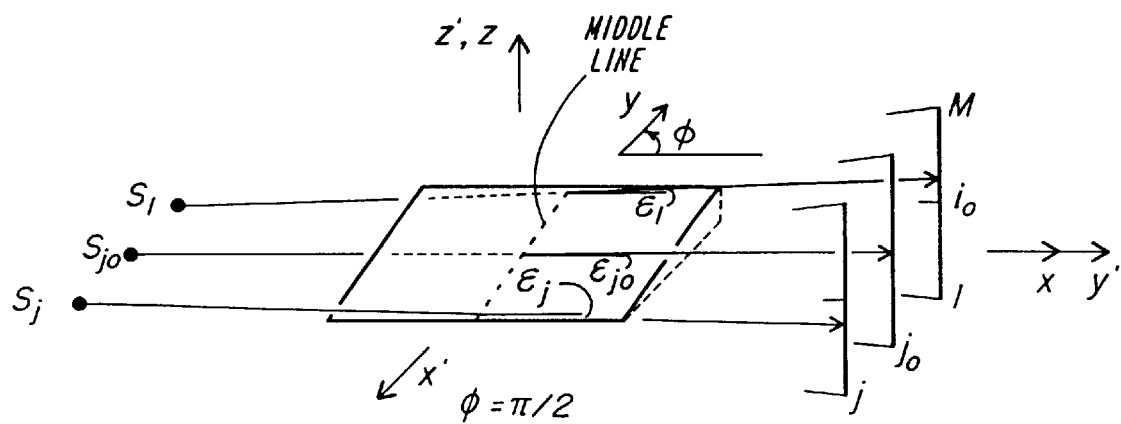

The magnitude of the aberration angles from all channels indicates the closeness of the slice being coplanar with the rays. The optimal slice for reconstruction is the one with the smallest aberration angles. An oblique slice can have smaller aberration angles than the normal slice. The aberration angle $\epsilon_j$ of an oblique slice is shown in FIG. 9A at view angle of $\phi=0°$, and in FIG. 9B at a view angle of $\phi=90°$. As shown in FIG. 9A, the aberration angles of an oblique slice at a view angle of $\phi=0°$ are less than those of a normal slice. As shown in FIG. 9B, the aberration angles of the oblique slice at a view angle of 90° are also smaller than those of the normal slice.

For ease of understanding of the description, reconstruction of only one oblique slice will be described. It will be understood that the description can be extended to any number of slices. Let (u,v) be a rectilinear coordinate on the slice with u-axis being the line intersected by the xy-plane. The oblique slice can be considered to be the result of rotating a normal slice about the u-axis for an angle α. The angle α is the oblique angle of the slice.

Figure 10A:
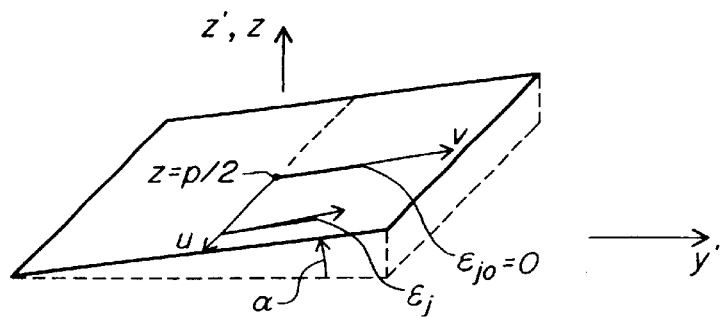
FIGS. 10A, 10B and 10C are schematic diagrams illustrating an oblique slice in accordance with the invention at view angles of 0, 90 and 180 degrees, respectively.

An oblique slice in accordance with the invention at view angle of φ=0° is depicted in FIG. 10A, where the oblique angle α is the angle between v-axis and y'-axis. In one embodiment, it is preferred to select the oblique angle α such that the v-axis is coincident with a ray of the central longitudinal fan. In that case, the aberration angle of the central channel is zero, i.e., $\epsilon_{jo}=0$. The oblique slice is selected at a center location of p/2 with a slope of tan α in the +y' direction. Because the z position of any other longitudinal fan is offset from the central longitudinal fan by $d_j$ given in Equation (3) in the reordered parallel-beam geometry, the aberration angle of other channels are non-zero. Nevertheless, they are small and get smaller as the channel is closer to the central channel. The aberration angle $\epsilon_j$ of a channel j far away from the central channel is depicted in FIG. 10A.

Figure 10B:
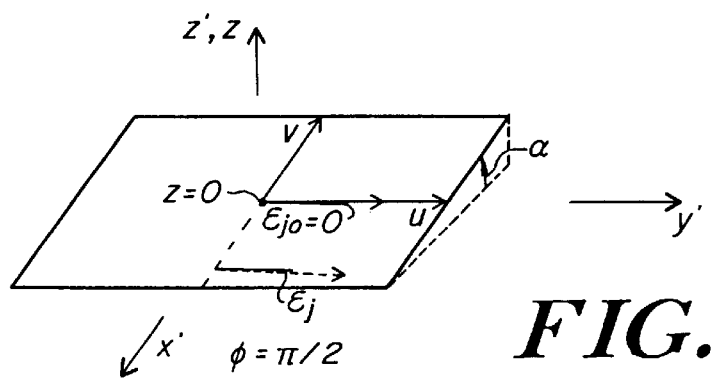

At a pitch of 2p for the helical scan, the oblique slice is preferably selected at a location along the z axis with its center at z=p/2. Then, at a view angle of φ=π/2, the center of the slice will have traveled by p/2 to the location of the isocenter as shown in FIG. 10B. The oblique slice is traveled to z=0 with the slope tan α in the −x' direction. The u-axis becomes coincident with the central ray of the central longitudinal fan. Again, the aberration angle of the central channel is zero, $\epsilon_{jo}=0$, while other channels $\epsilon_j \neq 0$.

Figure 10C:
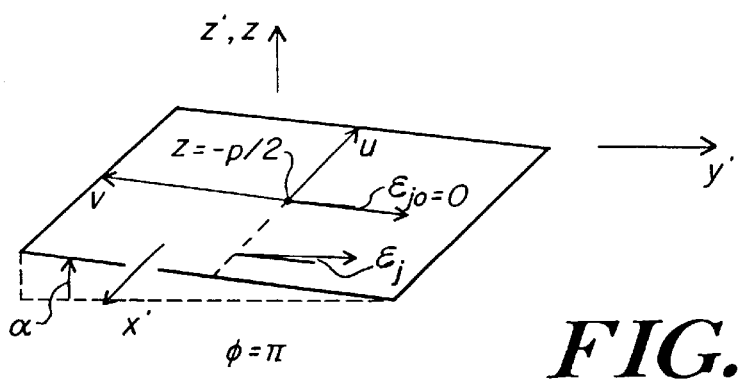

At a view angle of φ=π, the geometry of the oblique slice is as shown in FIG. 10C. Here, the v-axis becomes coincident with another ray of the central longitudinal fan and $\epsilon_{jo}=0$. The oblique slice has traveled a distance p. The oblique slice is further traveled to z=−p/2 with the slope tans in the −y' direction. For reconstructing the image from a half scan, the data at view angle φ=π is redundant with that at view angle φ=0. The figure is shown here for better demonstration of the oblique slice, in general the projection data of the oblique slice at φ=π are not needed.

It should be noted that when an oblique slice is coincident with a ray of the central longitudinal fan the focal spot is lying on the slice plane. In that case, the oblique slice will be coplanar with a transverse fan containing this ray. Therefore the oblique slice shown in FIG. 10 is coplanar with a transverse fan of the divergent cone-beam data a rotation angles of θ=0, π/2, and π.

It is not necessary to choose the oblique slice with exactly a null aberration angle at the central channel at φ=0, φ=π/2, and φ=π. Any oblique slice close to the oblique angle described here is acceptable. As can be seen from the figures, the oblique angle α is roughly equal to one half the cone angle, that is, $\alpha \approx \beta_{max}$. In fact, α is preferably less than $\beta_{max}$, because the pitch 2p is usually shorter than the z dimension of the detector array at the isocenter.

Figure 11:
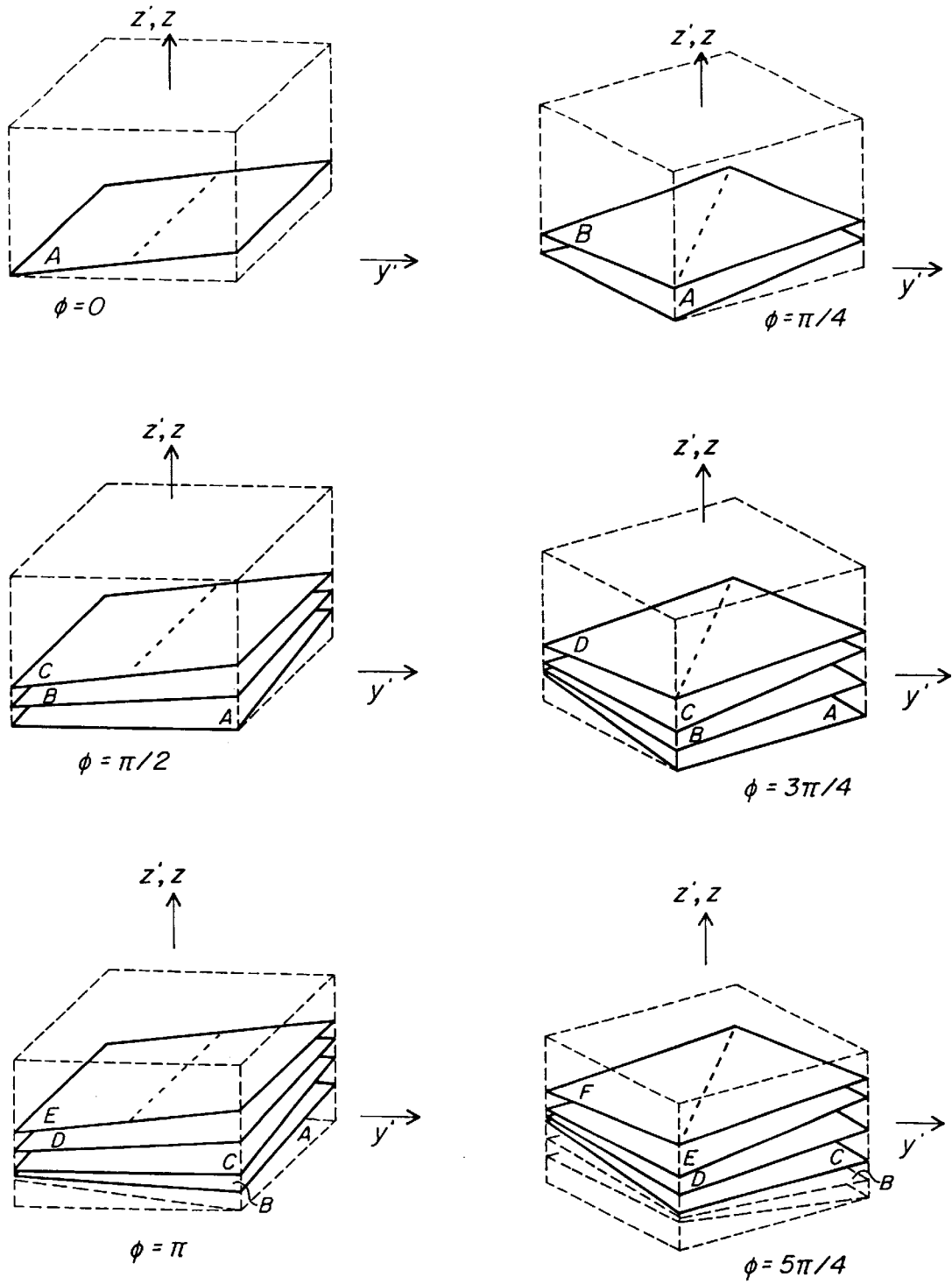
FIG. 11 schematically illustrates formation of a stack of oblique slices at multiple view angles in accordance with the invention.

In practice, multiple oblique slices at successive locations in the z direction are selected for reconstruction. As an example, assume four slices are selected over the length ofp in the z dimension. Once a slice is selected, its projection profiles are interpolated from the reordered data over the next 180° view angles. At view angle φ=0, the first slice A is selected as illustrated in FIG. 10A and reproduced in FIG. 11. At view angle φ=π/4, the second slice B is selected as if it were at zero view angle as in FIG. 10A. In the meantime, the first slice has traveled for p/4 and oriented at an azimuth angle of 45° with respect to the rotating frame x'y'z, as shown in FIG. 11 for φ=π/4. Similarly, the third slice C and forth slice D are selected at view angle of φ=π/2 and φ=3π/4, respectively, as if they were at zero view angle. At view angle φ=π, the fifth slice E is selected, while the interpolation for the projection profiles of first slice A has been completed.

From there on, at every π/4 interval one new slice is selected and one slice has completed the π view angle range as shown in the instance φ=5π/4 of FIG. 11. Thus, there are four slices for the interpolation of projection profile at each view angle starting from φ=3π/4. These four slices are located over the lengthp in the z dimension.

In general, if m oblique slices are required for the interpolation at each view angle, the interval of view angle to select a new slice is π/m. Let $\Phi_k$ be the view angle where the k slice is first selected as if it were at zero view angle, we have $$\Phi_k = k\pi/m \tag{4}$$

with k=0, 1, 2, . . . , $m_k$−1, and $m_k$ is the total number of slices to be selected over the whole length of the object. At the view angle of φ=π−π/m and thereafter, there will be m slices within the length p at each view angle. Given a view angle φ, these m slices are the slices with $\Phi_k$ in the range of $\phi - \pi < \Phi_k \leq \phi$. They all have the same oblique angle α. However they are separated by a constant distance of p/m along the z-axis, and oriented at different azimuth angles of π/m apart.

The selected oblique slices are not exactly coplanar with the rays. With the exception of a few rays in a few view angles, no ray is exactly coincident with the oblique slice. For each channel, the ray intersecting the center location of the slice is considered as the one nearest to the slice, and it is the ray to be interpolated from the original rays measured by the detector array. The intersecting points of these nearest rays for the N channels lie on a line on the slice, which is referred to as the middle line. In order to interpolate the nearest ray from the original rays for each channel, the location of the middle line in the rotating frame must be known at each view angle.

In the reordered parallel-beam geometry, the projection data $P_{ij}(\phi)$ can be considered as consisting of N longitudinal fans, as shown in FIG. 7. The rays of longitudinal fan j lie on an y'z'-plane parallel to that of the central longitudinal fan $j_o$, but separated by a distance of r sin(j−$j_o$)δ in the x' direction. The longitudinal fan j is also offset from the central longitudinal fan $j_o$ by $d_j$ in z' direction and by r−$a_j$ in the y' direction, as described above. The middle line of the oblique slice k is perpendicular to the longitudinal fan j. It is lying on the x'z'-plane with y'=0. Given the oblique angle α and the view angle φ, the slope of the middle line on the x'z'-plane can be determined. Based on the slope, the z position of the middle line at channel j can be derived from the z position of the middle line at the central channel $j_o$.

Firstly, since the oblique slices are separated by p/m and translating along z-axis at the rate of distancep over view angle of π, the z position of the middle line at the central channel can be written as $$z_{kjo} = z_o + kp/m - \phi p/\pi \tag{5}$$

where $z_o$ is a constant representing the z position of the first slice at starting view angle of φ=0, and k is the slice number with k=0, 1, 2, . . . , $m_k$−1. Secondly, in order to find the slope of the middle line, we start with the simple geometry of the oblique slice when it was selected at φ=$\Phi_k$. As can be seen from FIG. 10A and the φ=0 diagram of FIG. 11, the slope of the oblique slice is tan α along the y' direction. Thus, the z' coordinate of the oblique slice at $\phi=\Phi_k$ can be written as $$z'(\Phi_k)=z_{kjo}+y'\tan\alpha. \qquad (6)$$

The middle line is the line of y'=0 on the slice. We see that the middle line at $\phi=\Phi_k$ has a constant coordinate of $z'=z_{kjo}$, and the middle line is parallel to the x' axis as shown in FIG. 10A.

At a subsequent view angle of $\phi>\Phi_k$, the middle line can be located by rotating the oblique slice about the z'-axis for an angle of $\phi-\Phi_k$ and set the y' coordinate to 0. When the oblique slice is rotated about the z'-axis for $\phi-\Phi_k$, the z' coordinate of the oblique slice becomes $$z'(\phi)=z_{kjo}-x'\tan\alpha\sin(\phi-\Phi_k)+y'\tan\alpha\cos(\phi-\Phi_k). \qquad (7)$$

The middle line is given by Equation (7) with y'=0. In addition, we know that the x' coordinate of the middle line is $r\sin(j-j_o)\delta$ for channel j. Thus, by further setting $x'=r\sin(j-j_o)\delta$ to Equation (7), we have the z position of the middle line at channel j as $$z_{kj}(\phi)=z_{kjo}-r\tan\alpha\sin(\phi-\Phi_k)\sin((j-j_o)\delta). \qquad (8)$$

for the oblique slice k at a view angle of $\phi>\Phi_k$. Using Equation (5) for $z_{kjo}$, it becomes $$z_{kj}(\phi)=z_o+kp/m-\phi p/\pi-r\tan\alpha\sin(\phi-\Phi_k)\sin((j-j_o)\delta). \qquad (9)$$

This point of the middle line is intersected by the ray to be interpolated. Thus, $z_{kj}(\phi)$ is also considered as the z position of the interpolated ray. In general, the z position of a ray interpolated from a longitudinal fan on y'z'-plane is defined by the z coordinate of the ray at y'=0.

Figure 12:
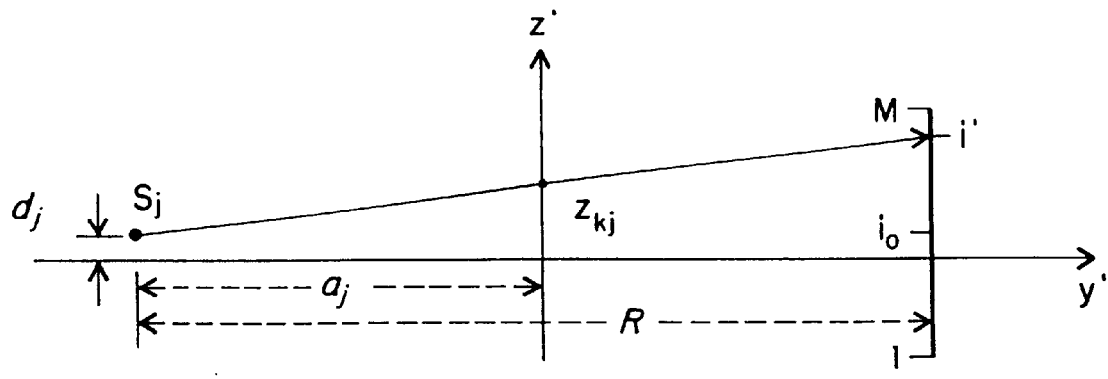
FIG. 12 schematically illustrates a ray to be interpolated from a longitudinal fan in accordance with the invention.

To interpolate a ray from the longitudinal fan, we notice that the oblique slice k is measured by the detector array for view angles between $\phi=\Phi_k$ and $\phi=\Phi_k+\pi$. Within that angular range, the corresponding detector row number of the ray intersecting the middle line is related to the z position $z_{kj}(\phi)$ by $$i'=i_o+(z_{kj}-d_j)R/\alpha_j. \qquad (10)$$

assuming $z_{kj}$ and $d_j$ are measured in terms of the number of rows of detectors. The geometry of the ray with respect to the longitudinal fan j is shown in FIG. 12, where $i_o$ is the central row number and R is distance from the focal spot $S_j$ to the column of M detectors. The value i' in Equation (10) is not an integer number. It can be written as the sum of a truncated integer q and a fractional part f $$i'=q+f \qquad (11)$$

with $0\leq f<1$. If a linear interpolation method is used to interpolate for the projections of the oblique slice, the interpolated projection value $P_{i'j}(\phi)$ for channel j will be calculated as $$P_{i'j}(\phi)=(1-f)P_{qj}(\phi)+fP_{q+1,j}(\phi). \qquad (12)$$

Although linear interpolation provides a method of obtaining the projection value $P_{i'j}(\phi)$, it is not the only possible choice for the interpolation. For example, if the slice width is greater than the height of one detector (length along z-axis), the data can be oversampled in the z dimension. A resampling method, such as the approach described in a copending U.S. patent application Ser. No. 09/375,151 entitled, "An Improved Cone-Beam CT System With Oversampling Detector Array and Resampling Technique," by C. M. Lai, filed on even date herewith, assigned to the same assignee as the present application and incorporated herein by reference, can be used to calculate for the projection value $P_{i'j}(\phi)$.

There are N projection values $P_{i'j}(\phi)$ to be calculated at each view angle. The rays of these interpolated projections are approximately coplanar with the oblique slice. Thus, the interpolated projections are taken as the projections of the oblique slice for 2D reconstruction of the slice's image. It is convenient to denote $P_{i'j}(\phi)$ as $P_{kj}(\phi)$, to indicate that $P_{i'j}(\phi)$ are used as the projection data of the oblique slice k. That is, $$P_{kj}(\phi)=P_{i'j}(\phi) \qquad (13)$$

with $k=0, 1, \ldots, m_k-1$, and $j=1, 2, \ldots, N$. At view angle $\phi$, there are m oblique slices, each with $\Phi_k$ in the range of $\phi-\pi<\Phi_k\leq\phi$, measured by the detector array. Thus, there are mN projection values $P_{kj}(\phi)$ to be interpolated for m slices in N channels at each view angle.

Figure 13:
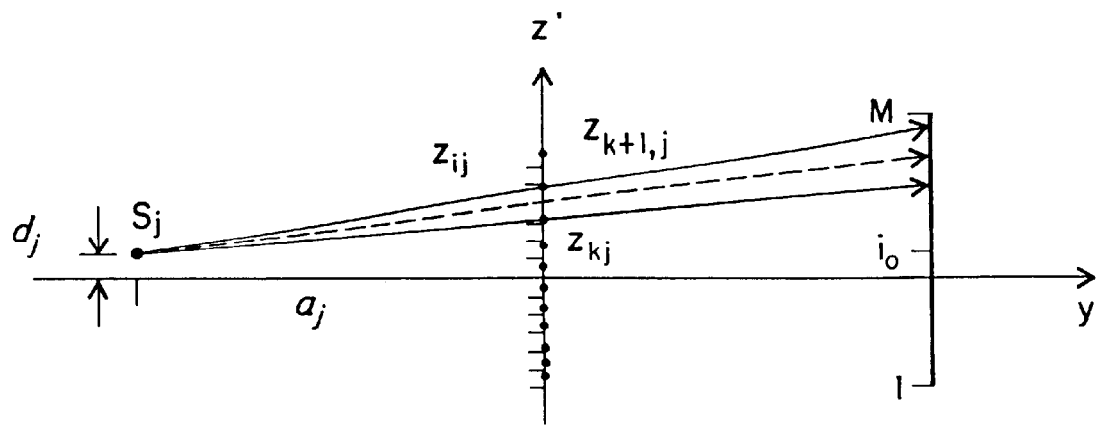
FIG. 13 schematically illustrates calculation of a projection value of a slice using a weighted sum of projection values of plural rays intersecting the slice, in accordance with the invention.

Although it is a good approximation to use $P_{i'j}(\phi)$ of the ray intersecting the middle line as the projection value $P_{kj}(\phi)$ of the slice k at channel j as described above, other methods of generating $P_{kj}(\phi)$ are possible. One method is to compute $P_{kj}(\phi)$ as a weighted sum of the projection values of all the rays intersecting the oblique slice at different y' locations as illustrated in FIG. 13.

Assuming the maximum number of rays to be used for the weighting is five, separated by an equivalent row number of τ. The central ray intersects the middle line of the oblique slice with projection value of $P_{i'j}(\phi)$. The weighted projection value for the channel j of slice k is calculated as $$P_{kj}(\phi)=w_0P_{i'j}(\phi)+w_1P_{i'+\tau,j}(\phi)+w_2P_{i'-\tau,j}(\phi)+w_3P_{i'+2\tau,j}(\phi)+w_4P_{i'-2\tau,j}(\phi). \qquad (14)$$

The weighting factors depend on the aberration angle $\epsilon_j$ and the relative z-position of the middle line with respect to the focal spot. They vary with the channel j and the view angle $\phi$. In general, we have $$w_0+w_1+w_2+w_3+w_4=1 \qquad (15)$$

with $w_2\cong w_1$, $w_4\cong w_3$, and $w_0\geq w_1\geq w_3$. In this case, five projection values are interpolated or re-sampled from the collected projections $P_{ij}(\phi)$ for each channel. The weighting factors can be combined with the coefficients in the interpolation or re-sampling process, such that $P_{kj}(\phi)$ can be computed directly from the collected data $P_{ij}(\phi)$ as $$P_{kj}(\phi)=w_0P_{qj}(\phi)+w_1P_{q+\tau,j}(\phi)+w_2P_{q-\tau,j}(\phi)+w_3P_{q+2\tau,j}(\phi)+w_4P_{q-2\tau,j}(\phi) \qquad (16)$$

where q is the truncated integer of i' as described in Equation (11). The weighting factors here are further depending on difference between i' and q, and the relations $w_2\cong w_1$, $w_4\cong w_3$, and $w_0\geq w_1\geq w_3$ are not necessarily valid.

The example given here is a 5-term weighted projection value for the oblique slice. In practice, the spacing τ and the number of terms included for the weighting can be varied.

At each view angle, m projection profiles are interpolated for the m slices measured by the detector array. Each projection profile contains N projection values $P_{kj}(\phi)$, with $j=1, 2, \ldots, N$ for oblique slice k. The rays of these N projection values are separated by a variable spacing in the lateral dimension (the x' dimension). This is because the longitudinal fan j is at a nonlinear distance of $r\sin\gamma_j=r\sin((j-j_o)\delta)$ from the central longitudinal fan $j_o$, as shown in FIGS. 5 and 7.

For the subsequent convolution operation, it is required that these projection values are sampled at a constant lateral spacing. Therefore, the projection data $P_{kj}(\phi)$ are interpolated into equal lateral spacing at every view angle, like the parallel-beam projection data of a conventional single detector system. The lateral spacing at the central channel is r sin $\delta \approx r \delta$. If r $\delta$ is chosen as the constant spatial interval for all channels, the projection data $P_{kj}(\phi)$ will be interpolated into a constant spacing of r $\delta$. The interpolation is performed among the N channels of each slices, independent of other slices.

This equal lateral spacing interpolation can also be performed on the original data $P_{ij}(\phi)$ collected by each row of detectors, before they are used to calculate the projection values of the oblique slices. In that case, the parallel projections $P_{ij}(\phi)$ reordered from each row are interpolated into equal lateral spacing of say r $\delta$. With the N channel in equal spacing, the z position of the channel j in Equation (9) becomes $$z_{kj}(\phi)=z_o+kp/m-\phi p/\pi-r \tan \alpha \sin(\phi-\Phi_k)(j-j_o)\delta. \quad (17)$$

Based on the equal spaced $P_{ij}(\phi)$ and Equation (17), the projection data $P_{kj}(\phi)$ interpolated to the oblique slice k will have equal lateral spacing of r $\delta$.

The N projection values of $P_{kj}(\phi)$ at equal spacing are then convoluted with a well-known convolution kernel for reconstruction of a 2D image. The convolution is performed at each view angle for each slice, in the same manner as in a convention system with single row of detectors. Let the convoluted projection value be $Q_{kj}(\phi)$ The convoluted projections $Q_{kj}(\phi)$ have equal spacing of r $\delta$ between adjacent channels. Whether this equal lateral spacing is performed before or after the generation of oblique-slice projections $P_{kj}(\phi)$, the z position of the convoluted projection $Q_{kj}(\phi)$ is given by $z_{kj}(\phi)$ in Equation (17), where the N channels are at a constant lateral spacing of r $\delta$.

The constant lateral spacing r$\delta$ is measured on the xy plane and remains the same constant for all view angles. When these convoluted data are backprojected to a 2D image matrix, the elements of the matrix are located at equally spaced (x,y) coordinates. The reconstructed image can be considered as the image of the oblique slice projected onto the xy-plane.

The oblique slices are not necessarily parallel to each other. Although a stack of such oblique slices contain the full information of the volumetric image, it is generally preferred to store and display the volumetric image as a stack of normal slices. The location and orientation of the oblique slices are precisely known. Thus the image intensity of the normal slices can be interpolated from the reconstructed oblique slices along the z direction. The z coordinates of the oblique slices can be obtained by setting $\phi=0$ to Equation (7). At $\phi=0$, the rotating frame (x',y',z') is coincided with the laboratory frame (x,y,z), and we have $$z=z_{kjo}+x \tan \alpha \sin \Phi_k+y \tan \alpha \cos \Phi_k. \quad (18)$$

Equation (18) indicates that at the same xy-location, the z coordinates of the oblique slices are not equally spaced. It can be time consuming to find the oblique slice nearest to the normal slice in the z direction. Therefore, it is preferred to pre-calculate the index and the z coordinate of the oblique slice nearest to the normal slice at each pixel location, and store them into a lookup table for interpolating the image intensity of the normal slice.

Each normal slice has one lookup table for the interpolation. However, one lookup table can be shared for multiple slices. This is because sin $\Phi_k$ and cos $\Phi_k$ in Equation (18) are periodical functions of k with a period of 2m, as can be seen from Equation (4). When 2m oblique slices are grouped for the interpolation, the relative z locations with respect to the corresponding group of normal slices are the same for all groups. Thus, the total number of different lookup tables is no more than 2m. Furthermore, the look tables of the first m slices can be used to interpolate for the second m slices. In that case, the second m slices will be 180° rotated about the z-axis with respect to the first m slices. The 180° rotation of the images can be easily rectified. Therefore, the total number of lookup tables can be reduced to m, which is usually much smaller than total number of slices $m_k$.

Although the embodiments of the CT scanner are described and shown as third generation types, wherein the detectors and x-ray source rotate about the longitudinal axis, other generation machines, such as fourth generation machines, wherein the x-ray source rotates about the longitudinal axis while the x-ray detectors remain fixed relative to the gantry frame, can also possibly be used.

While this invention has been particularly shown and described with references to preferred embodiments thereof, it will be understood by those skilled in the art that various changes in form and details may be made therein without departing from the spirit and scope of the invention as defined by the following claims.

What is claimed is:

1. A method of reconstructing image data for a region having a longitudinal axis, comprising:
    providing a radiation source and an array of detectors on opposed sides of the region, the radiation source emitting radiation toward the array of detectors to generate a plurality of diverging radiation beams received by the array of detectors, at least one of the radiation source and the array of detectors being rotatable about the longitudinal axis through a plurality of projection angles to scan the region to generate diverging beam scan data for the region;
    converting the diverging beam scan data for the region into parallel beam scan data for the region;
    defining at least one oblique image slice for the region, said oblique image slice being oblique with respect to the longitudinal axis; and
    using at least a portion of the parallel beam scan data for the region, generating image data for the at least one oblique image slice.

2. The method of claim 1 wherein the array of detectors is a two-dimensional array of detectors.

3. The method of claim 1 wherein the plurality of diverging radiation beams form a cone beam of radiation.

4. The method of claim 1 wherein the diverging beam scan data is obtained by helical cone beam scanning of the region.

5. The method of claim 1 wherein an angle formed by the oblique image slice and the longitudinal axis is selected such that the oblique image slice is coplanar with the radiation source for at least one projection angle.

6. The method of claim 1 wherein an angle formed by the oblique image slice and the longitudinal axis is selected such that the oblique image slice is coplanar with the radiation source for three projection angles.

7. The method of claim 6 wherein for the at least one oblique image slice, the three projection angles for which the oblique image slice is coplanar with the radiation source are 0 degrees, 90 degrees and 180 degrees.

8. The method of claim 1 wherein the image data for the at least one oblique image slice is generated using parallel beam scan data for a ray intersecting the at least one oblique image slice.

9. The method of claim 8 wherein the ray intersects the middle of the at least one oblique image slice.

10. The method of claim 1 wherein the image data for the at least one oblique image slice is generated using parallel beam scan data for a plurality of rays intersecting the at least one oblique image slice.

11. The method of claim 10 wherein the plurality of rays are weighted according to the locations at which they intersect the at least one oblique image slice.

12. The method of claim 1 further comprising generating image data for at least one normal image slice normal to the longitudinal axis using the image data for the at least one oblique image slice.

13. The method of claim 12 further comprising generating an image using the image data for the at least one normal image slice.

14. An apparatus for reconstructing image data for a region having a longitudinal axis, comprising:

a radiation source and an array of detectors on opposed sides of the region, the radiation source emitting radiation toward the array of detectors to generate a plurality of diverging radiation beams received by the array of detectors, at least one of the radiation source and the array of detectors being rotatable about the longitudinal axis to scan the region to generate diverging beam scan data for the region; and a processor for (I) converting the diverging beam scan data for the region into parallel beam scan data for the region, (ii) defining at least one oblique image slice for the region, said oblique image slice being oblique with respect to the longitudinal axis, and (iii) using at least a portion of the parallel beam scan data for the region, generating image data for the at least one oblique image slice.

15. The apparatus of claim 14 wherein the array of detectors is a two-dimensional array of detectors.

16. The apparatus of claim 14 wherein the plurality of diverging radiation beams form a cone beam of radiation.

17. The apparatus of claim 14 wherein the diverging beam scan data is obtained by helical cone beam scanning of the region.

18. The apparatus of claim 14 wherein an angle formed by the oblique image slice and the longitudinal axis is selected such that the oblique image slice is coplanar with the radiation source for at least one projection angle.

19. The apparatus of claim 14 wherein an angle formed by the oblique image slice and the longitudinal axis is selected such that the oblique image slice is coplanar with the radiation source for three projection angles.

20. The apparatus of claim 19 wherein for the at least one oblique image slice, the three projection angles for which the oblique image slice is coplanar with the radiation source are 0 degrees, 90 degrees and 180 degrees.

21. The apparatus of claim 14 wherein the processor generates the image data for the at least one oblique image slice using parallel beam scan data for a ray intersecting the at least one oblique image slice.

22. The apparatus of claim 21 wherein the ray intersects the middle of the at least one oblique image slice.

23. The apparatus of claim 14 wherein the processor generates the image data for the at least one oblique image slice using parallel beam scan data for a plurality of rays intersecting the at least one oblique image slice.

24. The apparatus of claim 23 wherein the plurality of rays are weighted according to the locations at which they intersect the at least one oblique image slice.

25. The apparatus of claim 14 wherein the processor generates image data for at least one normal image slice normal to the longitudinal axis using the image data for the at least one oblique image slice.

26. The apparatus of claim 25 wherein the processor generates an image using the image data for the at least one normal image slice.

* * * * *